(12) United States Patent
Pham et al.

(10) Patent No.: US 12,178,997 B2
(45) Date of Patent: Dec. 31, 2024

(54) FLOW INDICATOR FOR AN INFUSION PUMP

(71) Applicant: Avent, Inc., Alpharetta, GA (US)

(72) Inventors: Bao-Tram N. Pham, Irvine, CA (US); Justin Coker, Laguna Nigel, CA (US); Shane A. Duffy, Irvine, CA (US); Judith Davenport, Mission Viejo, CA (US); Kenneth C. Hsu, Tustin, CA (US); Ryan Massengale, Mission Viejo, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 18/358,229

(22) Filed: Jul. 25, 2023

(65) Prior Publication Data

US 2024/0017007 A1     Jan. 18, 2024

Related U.S. Application Data

(63) Continuation of application No. 16/918,273, filed on Jul. 1, 2020, now Pat. No. 11,752,261, which is a
(Continued)

(51) Int. Cl.
*A61M 5/168*     (2006.01)
*A61M 5/145*     (2006.01)
*A61M 5/14*      (2006.01)

(52) U.S. Cl.
CPC ...... *A61M 5/1684* (2013.01); *A61M 5/14586* (2013.01); *A61M 5/16886* (2013.01);
(Continued)

(58) Field of Classification Search
CPC .... A61M 2205/583; A61M 2205/3584; A61M 2205/3553; A61M 2205/3389;
(Continued)

(56) References Cited

U.S. PATENT DOCUMENTS 5,080,652 A   1/1992   Sancoff et al.
5,105,983 A   4/1992   Sancoff et al.
(Continued)

*Primary Examiner* — Kevin C Sirmons
*Assistant Examiner* — Alexandra Lalonde
(74) *Attorney, Agent, or Firm* — Meunier Carlin & Curfman LLC

(57) ABSTRACT

Systems and methods are provided for signaling a condition of an infusion assembly. An example system may comprise an elastomeric pump that includes a chamber for receipt of a volume of fluid, an outer layer configured to expand and contract as the chamber receives and dispenses the fluid, and a passive indicator provided on the outer layer for signaling a change in the volume of the fluid in the chamber. The example system further may comprise an image capture device configured to capture an image of the pump, and a processing system configured to process the image to signal the condition of the infusion assembly to a user of the system. An example method may comprise capturing the image of the pump; processing the image; and displaying information to the user of the pump to communicate a condition of the pump to the user. Various elastomeric pumps for infusion assemblies also are provided.

20 Claims, 6 Drawing Sheets

Related U.S. Application Data continuation of application No. 15/550,580, filed as application No. PCT/US2016/048258 on Aug. 24, 2016, now Pat. No. 10,737,023.

(52) U.S. Cl.
CPC ..... *A61M 2005/1405* (2013.01); *A61M 5/141* (2013.01); *A61M 2205/0216* (2013.01); *A61M 2205/3306* (2013.01); *A61M 2205/3334* (2013.01); *A61M 2205/3389* (2013.01); *A61M 2205/3553* (2013.01); *A61M 2205/3584* (2013.01); *A61M 2205/583* (2013.01)

(58) Field of Classification Search
CPC .. A61M 2205/3334; A61M 2205/3306; A61M 2205/584; A61M 2205/0227; A61M 2205/3317; A61M 2205/0216; A61M 2205/33; A61M 2205/3327; A61M 2205/35; A61M 2205/3546; A61M 2205/3576; A61M 2205/50; A61M 2205/502; A61M 2205/6063; A61M 2205/52; A61M 2205/60; A61M 5/1684; A61M 5/14586; A61M 5/152; A61M 5/16854; A61M 5/16886; A61M 5/172; A61M 5/168; A61M 5/14; A61M 5/141; A61M 5/142; A61M 5/145; A61M 5/14593; A61M 5/16831; A61M 5/148; A61M 5/16809; A61M 5/00; A61M 5/14224; A61M 5/14244; A61M 5/14248; A61M 5/1483; A61M 5/1486; A61M 5/16804; A61M 2209/045; A61M 2005/1405; A61M 2005/14204; A61M 2005/14208; A61M 2005/14288; A61M 2005/14292; A61M 19/00; A61M 1/00; A61M 1/77; H04N 7/188; G01L 11/02; G01N 2223/40; G01N 21/9081; G06T 7/0002; G06T 7/0004; G16H 20/13; G16H 20/17

See application file for complete search history.

(56) References Cited

U.S. PATENT DOCUMENTS

| | | |
|---|---|---|
| 5,254,481 A | 10/1993 | Nishida |
| 6,010,482 A * | 1/2000 | Kriesel .................... G01P 1/08 |
| | | 604/890.1 |
| 7,959,623 B2 | 6/2011 | Massengale |
| 2018/0306661 A1* | 10/2018 | Stacey .................... G01L 11/02 |

* cited by examiner

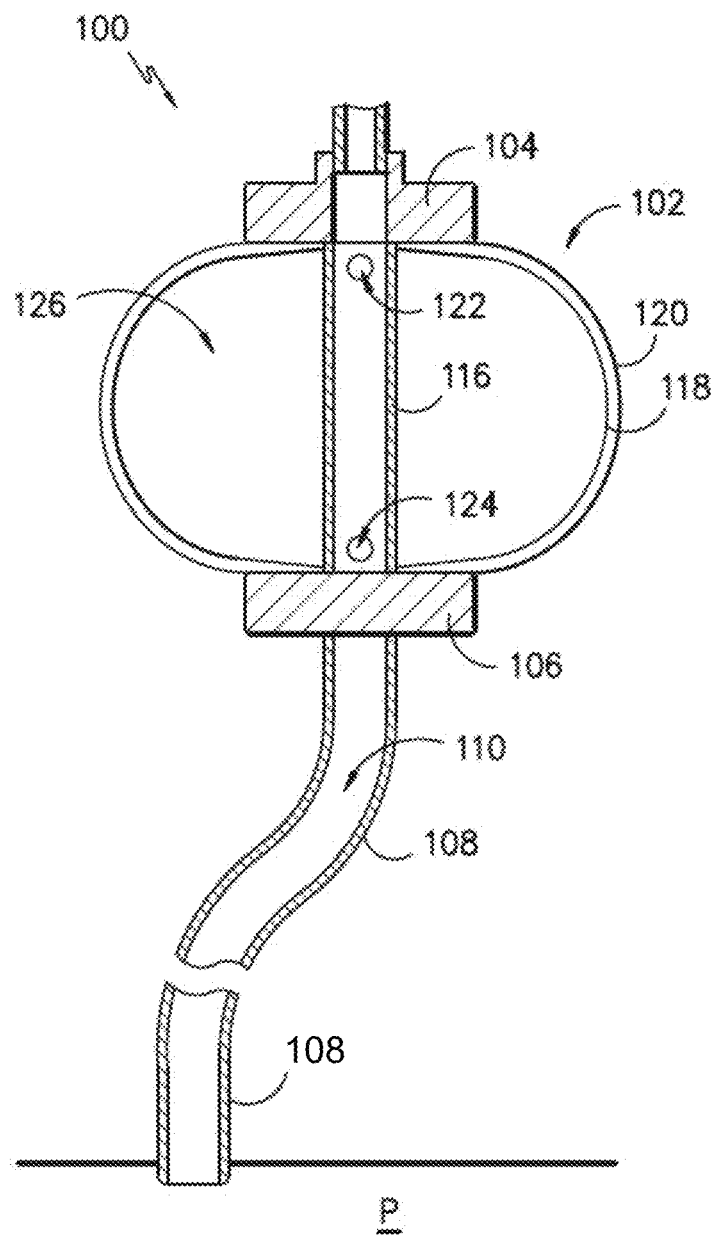
FIG. -1-

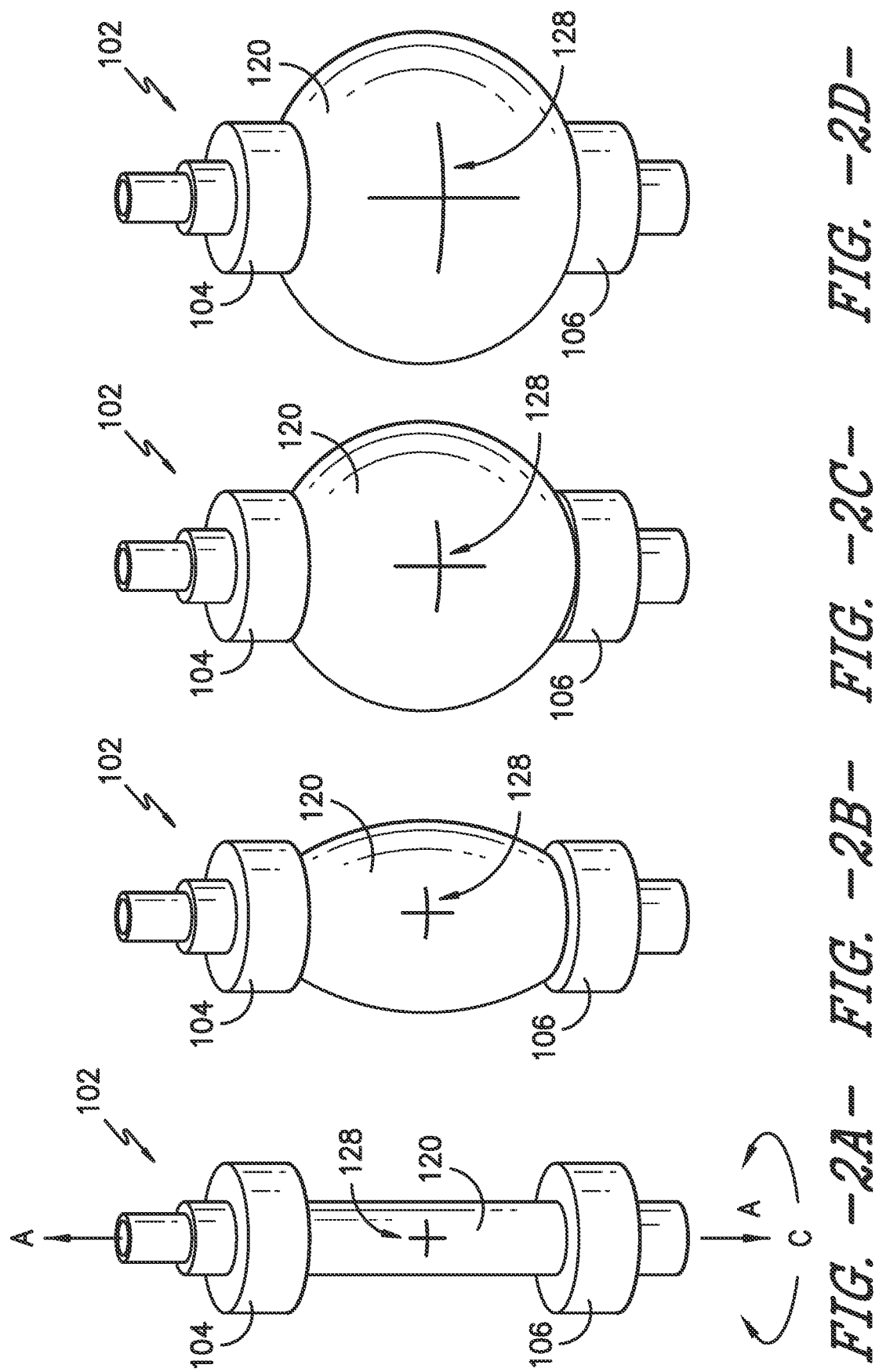

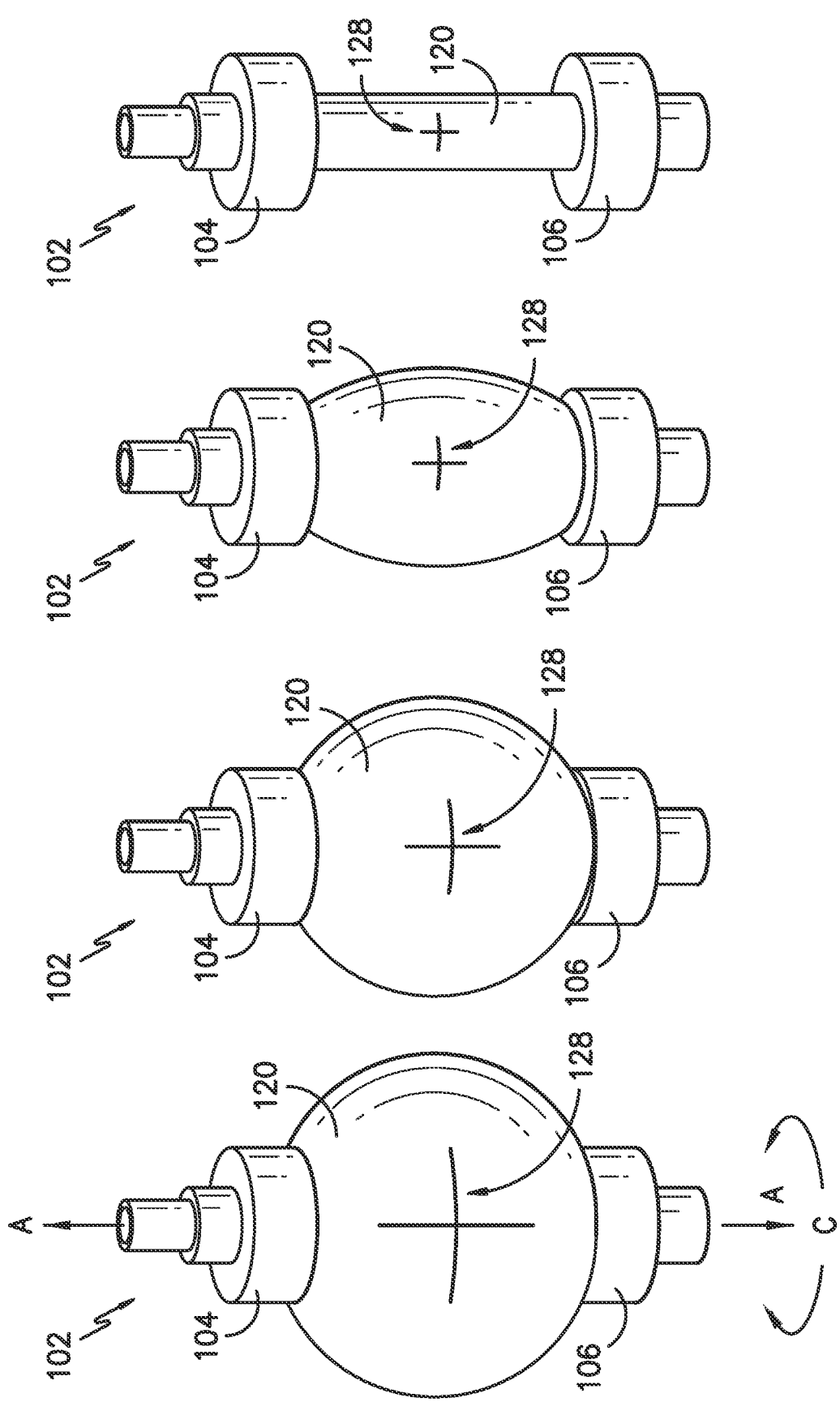

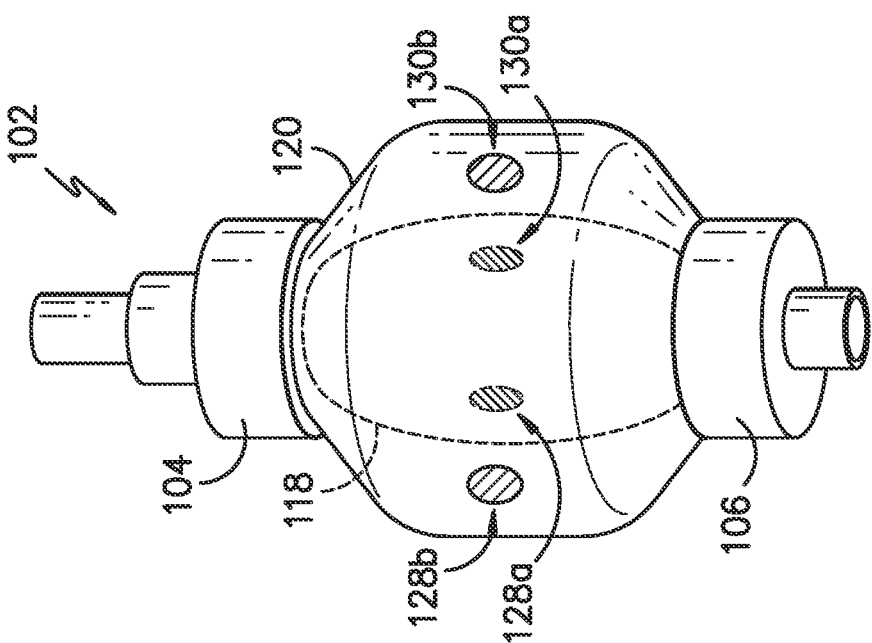
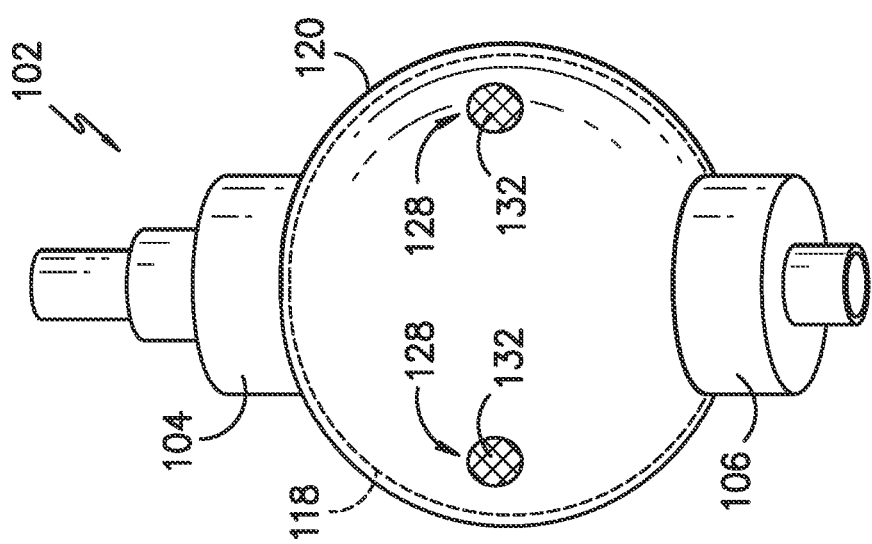
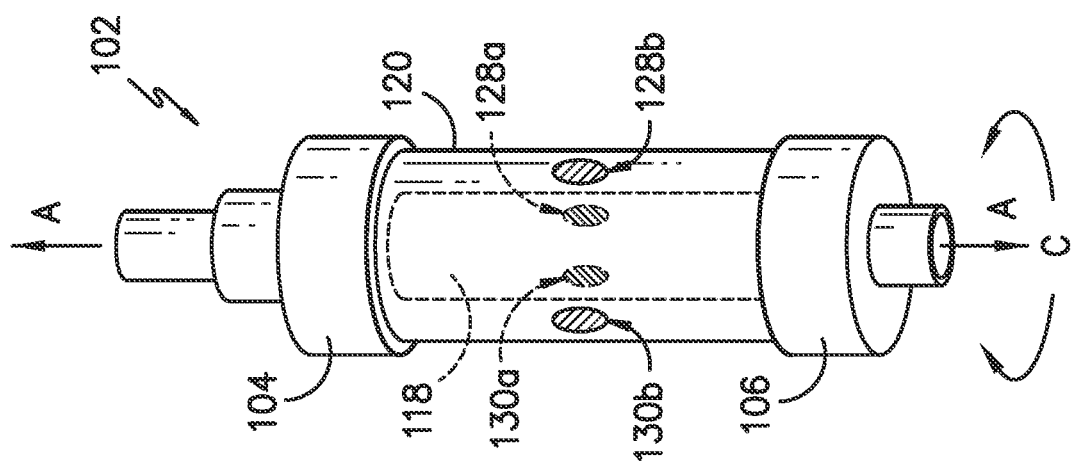

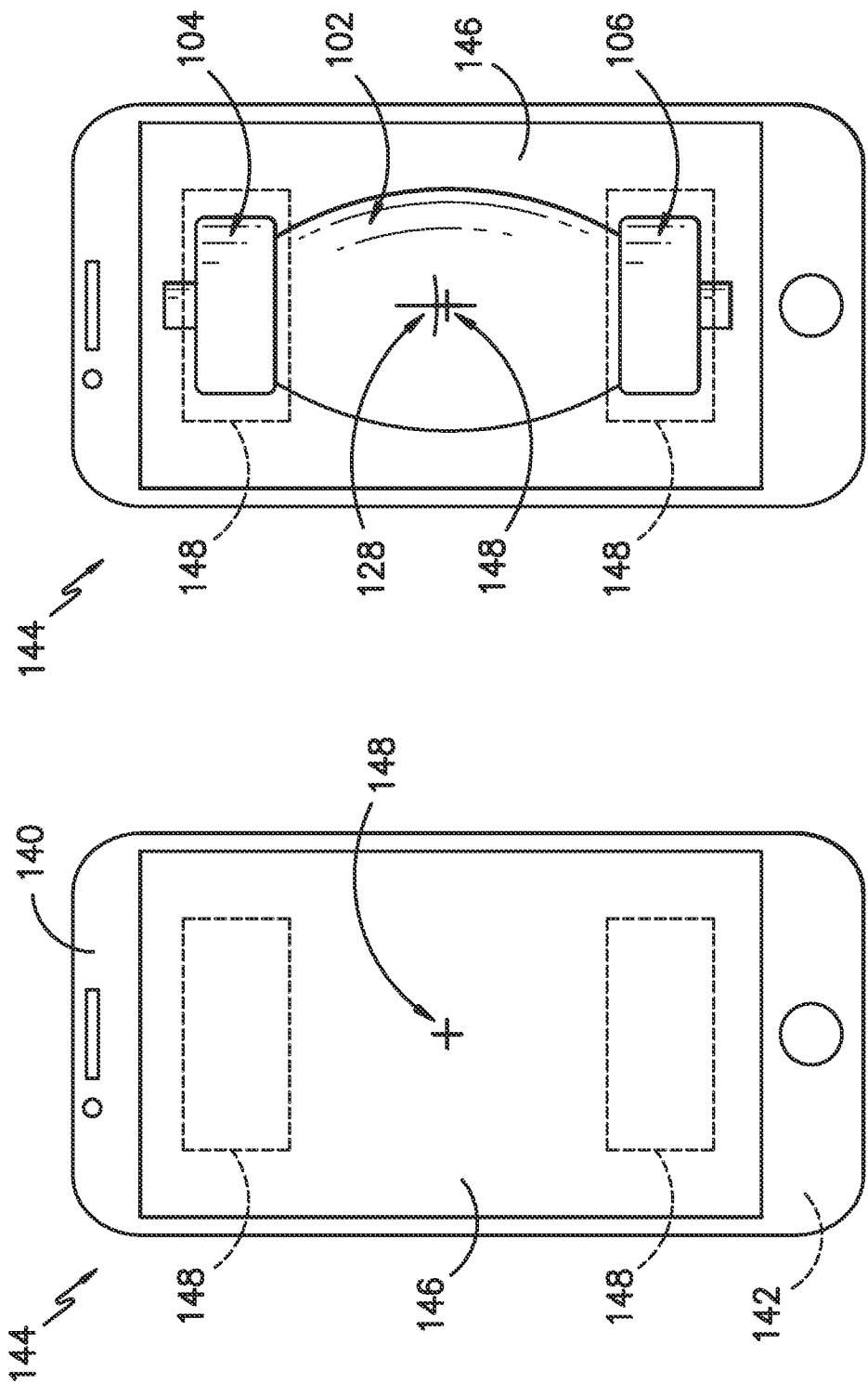

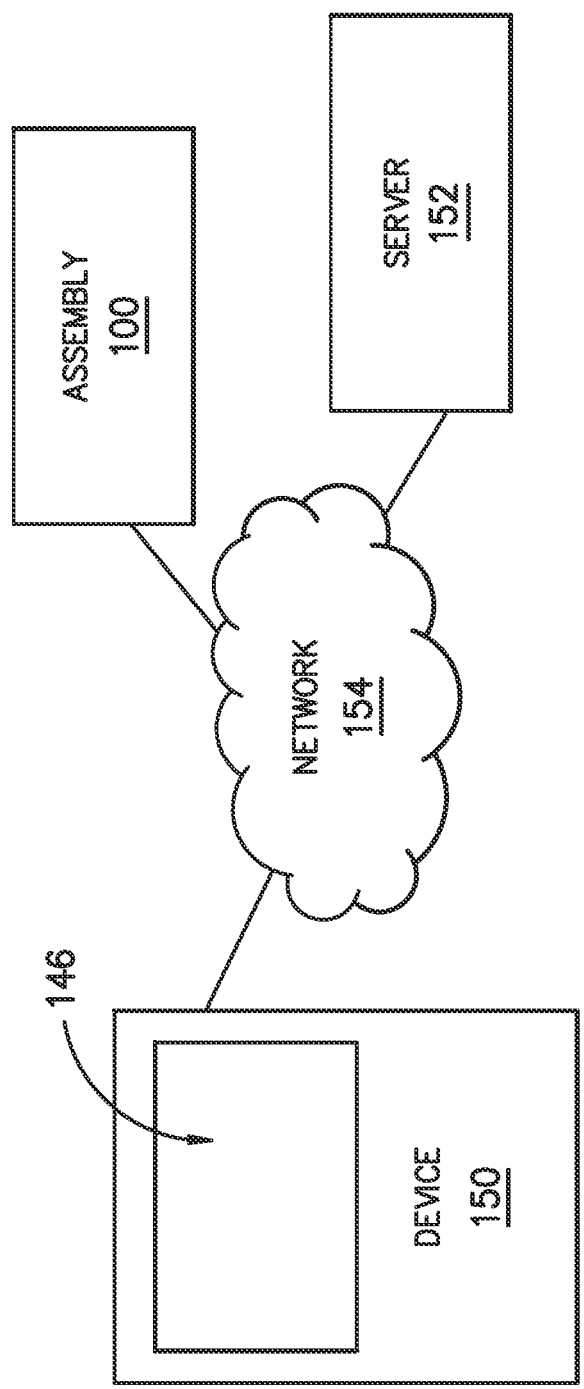
FIG. -6-

FLOW INDICATOR FOR AN INFUSION PUMP

CROSS-REFERENCE TO RELATED APPLICATIONS

This application is a continuation of U.S. application Ser. No. 16/918,273, filed Jul. 1, 2020, issued to U.S. Pat. No. 11,752,261, which is a continuation of U.S. application Ser. No. 15/550,580, filed Aug. 11, 2017, issued as U.S. Pat. No. 10,737,023, which is a national phase of and claims priority to PCT/US2016/048258, filed Aug. 24, 2016, all of which are incorporated herein by reference in their entries.

FIELD

The present disclosure relates to liquid dispensing apparatus and, more particularly, to an infusion apparatus or assembly for delivering intravenous drugs to a patient having an indicator for indicating the intravenous drugs are flowing from a pump of the apparatus.

BACKGROUND

It is often necessary to intravenously supply patients with pharmaceutically active liquids at a controlled rate over a period of time. Desirably, a patient remains in an ambulatory state while receiving the intravenous supply of pharmaceutically active liquids. Typical devices for accomplishing this purpose typically include an inflatable elastomeric bladder forming a liquid container and having a feature such as a flow control valve and tubing for supplying the liquid to the patient. The bladder has walls that are forced to expand when filled with the liquid and provide the pressure for expelling the liquid.

One drawback of conventional devices is that it is difficult for users, such as the patient or a caregiver, to discern whether the pump is providing the liquid, i.e., whether the device is dispensing liquid from the bladder. Accordingly, a device having an elastomeric pump and including features for indicating a change in volume of a bladder of the pump would be useful. Further, a device having an elastomeric pump that includes one or more features for communicating information about the operation of the pump based on an indicator for indicating a change in volume of a bladder of the pump would be beneficial. An indicator for indicating a change in volume of a bladder of an elastomeric pump that is easy to see and understand or interpret information indicated by the indicator would be desirable.

SUMMARY

Aspects and advantages of the disclosure will be set forth in part in the following description, or may be obvious from the description, or may be learned through practice of the disclosure.

In one aspect, the present subject matter is directed to a system for signaling a condition of an infusion assembly. The system comprises an elastomeric pump that includes a chamber for receipt of a volume of fluid, an outer layer configured to expand as the chamber receives fluid and to contract as the chamber dispenses fluid, and a passive indicator provided on the outer layer for signaling a change in the volume of fluid in the chamber. The system further comprises an image capture device and a processing system. The image capture device is configured to capture an image of the pump, and the processing system is configured to process the image to signal the condition of the infusion assembly to a user of the system.

In some embodiments, the system further comprises a display for providing the information to the user. The processing device may display a guide on the display to assist the user in utilizing the image capture device to capture the image. Further, in various embodiments, a single device may comprise the image capture device and the processing system.

In yet other embodiments, the indicator provided on the pump comprises an ink printed on the outer layer of the pump. The indicator may be a symbol, text, graphic, numeral, or other appropriate visual feature. In some embodiments, the indicator increases in size as the outer layer expands and decreases in size as the outer layer contracts.

Alternatively or additionally, the pump further comprises a bladder defining the chamber. The outer layer of the pump may surround the bladder. In some embodiments, a first indicator also is provided on the bladder such that the indicator provided on the outer layer is a second indicator, and the first indicator and the second indicator may be configured to align to signal a change in the volume of fluid in the chamber.

In another aspect, the present subject matter is directed to a method for communicating a condition of an elastomeric pump for an infusion assembly. The method comprises capturing an image of the pump; processing the image; and displaying information to a user of the pump to communicate the condition of the pump to the user.

In various embodiments, the pump includes a chamber for receipt of a volume of fluid; an outer layer that is configured to expand as the chamber receives fluid and to contract as the chamber dispenses fluid; and a passive indicator provided on the outer layer for signaling a change in the volume of fluid in the chamber. In other embodiments, capturing the image comprises capturing an image of the indicator on the outer layer of the pump. In yet other embodiments, processing the image comprises comparing the image to a stored image.

Additionally or alternatively, the communicated condition is a change in volume of the pump. In some embodiments, of the exemplary method a single device captures the image, processes the image, and displays the information to the user. In still other embodiments, capturing the image comprises aligning the pump with guides displayed on a display of a user device configured to capture images.

In still another aspect, the present subject matter is directed to an elastomeric pump for an infusion assembly. The pump comprises a chamber for receipt of a volume of fluid; an outer layer that expands as the chamber receives fluid and contracts as the chamber dispenses fluid; and an indicator provided on the outer layer. The indicator is a passive indicator for signaling a change in the volume of fluid in the chamber.

In some embodiments of the elastomeric pump, the indicator comprises an ink printed on the outer layer. In various embodiments, the indicator is a symbol, text, graphic, numeral, or other appropriate visual feature. The indicator may change size as the outer layer expands and contracts. In some embodiments, the pump also includes a bladder defining the chamber, and the outer layer surrounds the bladder. A first indicator may provided on the bladder such that the indicator provided on the outer layer is a second indicator. The first indicator and the second indicator may be configured to align to signal a change in the volume of fluid in the chamber.

These and other features, aspects, and advantages of the present disclosure will become better understood with reference to the following description and appended claims. The accompanying drawings, which are incorporated in and constitute a part of this specification, illustrate embodiments of the disclosure and, together with the description, serve to explain the principles of the disclosure.

BRIEF DESCRIPTION OF THE DRAWINGS

A full and enabling disclosure of the present disclosure, including the best mode thereof, directed to one of ordinary skill in the art, is set forth in the specification, which makes reference to the appended figures, in which:

FIG. 1 is a schematic cross-section view of an infusion assembly according to an exemplary embodiment of the present subject matter.

FIGS. 2A, 2B, 2C, and 2D are side views of an elastomeric pump having an indicator and illustrate the pump in various stages of filling with a fluid, according to an exemplary embodiment of the present subject matter.

FIGS. 3A, 3B, 3C, and 3D are side views of the elastomeric pump of FIGS. 2A through 2D and illustrate the pump in various stages of dispensing the fluid, according to an exemplary embodiment of the present subject matter.

FIGS. 4A, 4B, and 4C are side views of an elastomeric pump having an indicator and illustrate the pump in various stages of filling with and dispensing a fluid, according to an exemplary embodiment of the present subject matter.

FIG. 5A is a front view of a user smartphone device having a display according to an exemplary embodiment of the present subject matter.

FIG. 5B is a front view of the user smartphone device of FIG. 5A showing an elastomeric pump aligned with guides on the display, according to an exemplary embodiment of the present subject matter.

FIG. 6 is a schematic view of a communications system including an infusion assembly and a user device according to an exemplary embodiment of the present subject matter.

DETAILED DESCRIPTION

Reference now will be made in detail to embodiments of the disclosure, one or more examples of which are illustrated in the drawings. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment can be used with another embodiment to yield a still further embodiment. Thus, it is intended that the present disclosure covers such modifications and variations as come within the scope of the appended claims and their equivalents.

Moreover, the particular the naming of the components, capitalization of terms, the attributes, data structures, or any other programming or structural aspect is not mandatory or significant, and the mechanisms that implement the disclosure or its features may have different names, formats, or protocols. Also, the particular division of functionality between the various components described herein is merely exemplary and not mandatory; functions performed by a single component may instead be performed by multiple components, and functions performed by multiple components may instead performed by a single component.

FIG. 1 provides a side view of an infusion assembly, e.g., for dispensing a fluid to a patient, according to an exemplary embodiment of the present subject matter. As shown, the exemplary infusion assembly 100 includes an elastomeric pump 102 having an upper support member 104 and a lower support member 106. Infusion assembly 100 defines an axial direction A, and lower support member 106 is spaced apart from upper support member 104 along the axial direction A.

More particularly, pump 102 defines a reservoir that serves as a pressurized fluid source, holding medicinal fluid, such as local anesthetics, and providing a source of fluid under pressure. Pump 102 forces the medicinal fluid through a tubing or conduit 108. Conduit 108 forms a continuous flow path 110 for delivery of the medicinal fluid into a wound site nerve bundle or the blood stream of a patient P. In the depicted exemplary embodiment, conduit or tubing 108 defines an outlet (not shown) connecting the continuous flow path 110 to a catheter 112 that delivers the medicinal fluid to patient P. In such embodiments, conduit 108 and catheter 112 may together define continuous flow path 110 from pump 102 to patient P.

Further, in some embodiments, infusion assembly 100 may be configured to provide for bolus delivery. In such configurations, conduit 108 may split into a continuous or primary flow path and a controlled bolus flow path (not shown). Thus, medicinal fluid may be delivered into a wound site nerve bundle or the blood stream of patient P from pump 102 via the continuous or primary flow path or from a bolus delivery system via the controlled bolus flow path.

Pump 102 preferably accommodates a volume from about 100 to 600 ml of fluid under a pressure of about 10 to 15 psi. More particularly, pump 102 has an inner core 116 extending between upper support member 104 and lower support member 106 along axial direction A. Inner core 116 is surrounded by an elastomeric bladder 118 within an outer layer 120. Inner core 116 preferably has an inlet port 122, e.g., to fill bladder 118 with fluid, and an outlet port 124 in fluid communication with conduit 108, e.g., to dispense the fluid from bladder 118 to patient P through flow path 110. Fluid is held under pressure within elastomeric bladder 118 and flows from elastomeric bladder 118 into conduit 108 through outlet port 124, preferably flowing at a controlled and predictable rate. Alternatively, conduit 108 may be sized to serve as a flow restrictor. Further, elastomeric bladder 118 preferably is constructed from a resilient material that may comprise a variety of elastomeric compositions well known in the art, including vulcanized synthetic polyisoprenes, natural latex, natural rubber, synthetic rubber, silicone rubber, or the like.

Exemplary pumps are described in U.S. Pat. Nos. 7,959,623 and 5,254,481, which are hereby incorporated by reference. A variety of other conventional pumps also may be used. For example, the pumps described in U.S. Pat. Nos. 5,080,652 and 5,105,983, which are hereby incorporated by reference, may be used. As will be understood by those of skill in the art, other suitable electronic or mechanical pumps offered by other manufacturers may be used as well.

Referring now to FIGS. 2A through 2D, in the depicted embodiment of infusion assembly 100, bladder 118 extends from upper support member 104 to lower support member 106 and defines a circumferential direction C. As fluid is received within a chamber 126 (FIG. 1) defined by bladder 118, bladder 118 expands from a generally deflated position, as shown in FIG. 2A, to a generally inflated position, as shown in FIG. 2D. That is, bladder 118 is expandable and expands from the deflated position to the inflated position as fluid is introduced into chamber 126 through inlet port 122. Further, bladder 118 contracts from the inflated position to the deflated position as fluid is dispensed from chamber 126 through outlet port 124 and into flow path 110 defined by conduit 108. More particularly, bladder 118 in the deflated position has a generally cylindrical shape, a first circumference, and a first volume $V_1$. In the inflated position, bladder 118 has a generally spherical shape, a second circumference, and a second volume $V_2$. Second volume $V_2$ is greater or larger than first volume $V_1$. Of course, bladder 118 may have other shapes as well, but regardless of its shape, bladder 118 has a greater or larger volume in its inflated position than in its deflated position.

As described with respect to FIG. 1, pump 102 may be a two layer pump having an outer layer 120 surrounding bladder 118 such that bladder 118 is an inner layer of pump 102. As such, the outer layer 120 is positioned radially outward from the inner layer, bladder 118. Both the outer and inner layers may expand and contract as chamber 126 receives and dispenses fluid. More particularly, bladder 118 may expand as fluid is received in chamber 126, and the bladder may expand against outer layer 120 such that outer layer expands as the bladder 118 expands. Similarly, as bladder 118 contracts as fluid is dispelled from chamber 126, the outer layer 120 contracts. In some embodiments, outer layer 120 may be relatively loose when bladder 118 is fully contracted or empty. That is, the outer layer 120 may not fully conform to the shape of bladder 118 for all volumes and/or circumferences of bladder 118. Rather, the outer layer 120 may hang or be configured loosely about bladder 118 when bladder 118 is empty or has a relatively small volume, but as the bladder 118 expands as the volume of fluid within bladder 118 increases, the outer layer 120 may better conform to the shape of bladder 118 and more tightly or closely track the shape, volume, and/or circumference of the bladder.

Further, it will be appreciated that some patients may be sensitive to various materials, e.g., latex, such that it may be undesirable to form components of infusion assembly 100 from such materials. In one embodiment, bladder 118 (the inner layer) comprises a latex material and the outer layer 120 comprises an expandable non-latex material, such that the portion of pump 102 that patient P may come into contact with is not constructed using a latex material. In other embodiments, other materials may be used, and bladder 118 and outer layer 120 may be made from any suitable material and have any suitable configuration.

As depicted in FIGS. 2A through 2D, an indicator 128 may be provided on the outer layer 120 for indicating a change in volume of the bladder 118. For example, the indicator 128 may be a symbol, graphic, text, or other visual or optical feature that is printed, painted, applied, or otherwise provided on the outer layer 120. In the illustrated embodiment of FIGS. 2A through 2D, the indicator 128 is a symbol, more particularly, a plus sign ("+"), printed on outer layer 120 or incorporated into the material from which outer layer 120 is made. That is, indicator 128 may be provided on an outer surface of outer layer 120 or embedded within the material forming outer layer 120. In FIG. 2A, chamber 126 is essentially empty, i.e., does not contain an appreciable quantity of fluid such that bladder 118 has its smallest volume and outer layer 120 is in its most contracted or smallest state. In successive FIGS. 2B, 2C, and 2D, chamber 126 is filling with fluid until it is essentially full or has received the quantity or volume of fluid it is to receive for an infusion of fluid to patient P as shown in FIG. 2D. That is, for some infusion procedures, chamber 126 may not completely fill with fluid such that a quantity or volume of fluid less than a maximum quantity or volume that chamber 126 can accommodate is received in the chamber for dispensing to the patient. However, in other infusion procedures, chamber 126 may receive the maximum quantity or volume of fluid to dispense to the patient.

As illustrated in FIGS. 2A through 2D, as the chamber 126 fills with fluid, bladder 118 and outer layer 120 each expand, although bladder 118 and outer layer 120 do not necessarily begin to expand at the same moment or expand at the same rate. As the outer layer 120 expands, the indicator 128 provided on outer layer 120 also expands. In the exemplary embodiment shown in FIGS. 2A through 2D, where indicator 128 is a plus sign ("+"), the plus sign expands generally along the axial direction A and the circumferential direction C such that the plus sign changes in size along the axial and circumferential directions A, C with the addition of fluid into chamber 126. Thus, the change in size of the indicator 128 signals to a user of infusion assembly 100 a change in volume of the bladder 118, thereby indicating to the user that bladder 118 (more particularly, chamber 126 defined by bladder 118) is filling with fluid for dispensing to a patient.

Turning to FIGS. 3A through 3D, the dispensing of fluid from bladder 118, a reverse or opposite process from the filling process illustrated in FIGS. 2A through 2D, also may be visually indicated via indicator 128. More specifically, as fluid is dispensed from chamber 126, e.g., through outlet port 124, bladder 118 and outer layer 120 each contract, although each layer need not begin to contract at the same time or contract at the same rate. In any event, as fluid is dispensed from chamber 126 of bladder 118 to patient P, the chamber 126 transitions from a filled state to an empty state, such that bladder 118 transitions from a filled volume to an empty volume. As the fluid egresses from chamber 126 and bladder 118 and outer layer 120 contract, the indicator 128 on outer layer 120 contracts or grows smaller. In the exemplary embodiment shown in FIGS. 3A through 3D, where indicator 128 is a plus sign ("+"), the plus sign contracts generally along the axial direction A and the circumferential direction C such that the plus sign changes in size along the axial and circumferential directions A, C as fluid flows out of chamber 126. Thus, the change in size of the indicator 128 signals to a user of infusion assembly 100 a change in volume of the bladder 118, thereby indicating to the user that bladder 118 (more particularly, chamber 126 defined by bladder 118) is dispensing fluid to patient P.

In some embodiments, the fluid within chamber 126 may be dispensed at a relatively low flow rate, e.g., from about 0.5 to about 14 cubic centimeters of fluid per hour, although other flow rates may be used as well. When fluid is dispensed from bladder 118 at such low flow rates, it may be difficult for a user to perceive that fluid is flowing, e.g., by observing pump 102 without an indicator such as indicator 128. However, by incorporating indicator 128, the visual indication of the change in volume of the bladder 118 may be easier to perceive and interpret than other indications such that the user can perceive that the fluid is flowing from bladder 118 even if the flow rate is relatively low.

Although illustrated in FIGS. 2A through 2D and FIGS. 3A through 3D as a plus sign "+", it will be appreciated that indicator 128 may have other forms, shapes, or configurations in other embodiments of outer layer 120 and/or infusion assembly 100. Also, in other embodiments, indicator 128 may be provided in other locations on outer layer 120. That is, while FIGS. 2A through 2D and FIGS. 3A through 3D illustrate indicator 128 as located approximately at an axial midpoint of outer layer 120, in other embodiments indicator 128 may be provided at a higher or lower axial position on outer layer 120. In some embodiments, more than one indicator 128 may be provided on outer layer 120, e.g., such that an indicator 128 may be visible no matter the viewing angle or position of the user.

Turning now to FIGS. 4A through 4C, another exemplary embodiment of the present subject matter is illustrated. As represented in FIGS. 4A through 4C, outer layer 120 may include an indicator 128 that changes in color and/or pattern to signal a change in volume of bladder 118, e.g., to visually or optically indicate whether fluid is flowing from bladder 118 to patient P. More particularly, a first indicator 128a may be provided on bladder 118 and a second indicator 128b may be provided on outer layer 120. First indicator 128a has a first color and/or pattern 130a and, similarly, second indicator 128b has a first color and/or pattern 130b. It will be appreciated that the second indicator 128b is visible to a user of infusion assembly 100. As chamber 126 is filling with fluid as shown in FIG. 4A, first indicator 128a and second indicator 128b may be separated or unaligned such that the first color/pattern 130b of second indicator 128b is visible to the user. But as chamber 126 is filled, the indicators 128a, 128b are brought together or aligned to display a second color and/or pattern 132 to the user of infusion assembly 100. The second color/pattern 132 indicates chamber 126 is full of the fluid to be dispensed to the patient P. As the fluid flows from chamber 126 for dispensing to patient P, the layers 118, 120 separate or become unaligned such that the color and/or pattern of the indicator 128b on outer layer 120, which remains visible to the user, changes from the second color and/or pattern 132, which is displayed when the indicators 128a, 128b are aligned, to the first color and/or pattern 130b and thereby signals that the fluid is being dispensed from chamber 126.

In an exemplary embodiment, the first indicator 128a may be blue in color, i.e., the first color 130a of first indicator 128a may be blue, and the second indicator 128b may be yellow in color such that the first color 130b of second indicator 128b is yellow. When first and second indicators 128a, 128b are brought together and/or aligned, the blue and yellow indicators 128a, 128b appear green, i.e., the second color 132 is green in such an embodiment. As fluid is dispensed from chamber 126, bladder 118 and outer layer 120 separate, such that the second color 132 (green) is no longer visible but the first color 130b of second indicator 128b (yellow) is again visible to the user.

It should be understood that indicators 128a, 128b may have other colors, patterns, forms, shapes, or configurations in other embodiments. For example, in some embodiments, first indicator 128a may have a first pattern 130a and second indicator 128b may have a first pattern 130b. When bladder 118 is not full of fluid, e.g., as the chamber 126 is filling or as fluid is being dispensed from the chamber, the first pattern 130b of second indicator 128b is visible to a user. When bladder 118 is full of fluid, first indicator 128a is aligned with or brought together with second indicator 128b, and a second pattern 132, rather than the first pattern 130b of second indicator 128b, is visible to the user.

Also, in other embodiments, indicators 128a, 128b may be provided in other locations of infusion assembly 100. That is, while FIGS. 4A through 4C illustrate indicators 128a, 128b as located approximately at an axial midpoint of bladder 118 and outer layer 120, in other embodiments indicators 128a, 128b may be provided at a higher or lower axial position of bladder 118 and outer layer 120. In some embodiments, more than one first indicator 128a and more than one second indicator 128b may be provided, e.g., such that an indicator 128 may be visible to the user no matter the viewing angle or position of the user.

Similar to the embodiment shown in FIGS. 2A through 3D, the fluid within chamber 126 of the exemplary embodiment of FIGS. 4A through 4C may be dispensed at a relatively low flow rate, e.g., from about 0.5 to about 14 cubic centimeters of fluid per hour, although other flow rates may be used as well. When fluid is dispensed from bladder 118 at such low flow rates, it may be difficult for a user to perceive that fluid is flowing, e.g., by observing pump 102 without an indicator such as indicator 128. However, by incorporating first and second indicators 128a, 128b, the visual indication of the change in volume of the bladder 118 may be easier to perceive and interpret than other indications such that the user can perceive that the fluid is flowing from bladder 118 even if the flow rate is relatively low.

Referring to FIGS. 5A and 5B, in one embodiment, an image capture device 140 and a processing system 142 may be used with infusion assembly 100. The image capture device 140 and processing system 142 may allow a user to receive a plurality of information about infusion assembly 100, such as, e.g., the volume of pump 102, the average flow rate, and projected time of completion of the infusion procedure. In the exemplary embodiment shown in FIGS. 5A and 5B, the image capture device 140 and processing system 142 are incorporated into a single device, a smartphone 144 (i.e., a wireless mobile user device) having a display 146. Utilizing, e.g., the image capture feature(s) of smartphone 144 and display 146, a user may capture an image (i.e., take a picture) of pump 102, and processing system 142 of smartphone 144 then may deliver one or more pieces of information regarding the operation of pump 102.

For example, as shown in FIGS. 5A and 5B, processing system 142 may utilize a software application or app that helps the user capture the image of pump 102 by displaying one or more guides 148. That is, the user may open or activate the app on the user's device, e.g., smartphone 144. Next, e.g., upon selection of a particular mode or feature, the app may display guides 148 on display 146. The user may then utilize the guides 148 to position pump 102 within a field of view of the image capture device 140 of smartphone 144. The guides 148 may, e.g., help the user capture an image of pump 102 containing relevant features of pump 102 needed for processing system 142 to determine an operating condition of the pump 102, such as indicator 128. For example, if the user does not capture the upper and lower supports 104, 106 of pump 102, processing system 142 may be unable to determine that it has a useable image for accurately assessing an operating condition of pump 102. Thus, guides 148 may help ensure the user captures a useful image of pump 102, e.g., an image of indicator 128 on outer layer 120 of pump 102. However, while FIG. 5B depicts capturing an image of outer layer 120 extending between upper support 104 and lower support 106, in some embodiments the user need not capture upper and lower supports 104, 106. Nevertheless, in embodiments in which the indicator 128 may be used to determine an operating condition of pump 102, it will be appreciated that it may be helpful to capture a static, i.e., unchanging, portion of the pump as a reference point, e.g., for comparing successive images of the pump.

Based on the image captured by the user, processing system 142 may calculate the volume of pump 102 at the time the user captured the image and display the volume information to the user via display 146 of smartphone 144. The processing system 142 also may display other information on display 146, such as the starting volume and/or the time interval required to complete the infusion procedure, which may alert and/or reassure the user that the pump 102 is working and fluid is flowing from bladder 118. In some embodiments, processing system 142 may prompt the user, e.g., via a visual and/or audible signal of smartphone 144, to capture images of the pump 102 at various time intervals. Capturing images over time may help processing system 142 to provide more information and/or more accurate information regarding the operation of pump 142. As an example, comparing multiple images of the pump 102 taken over a time interval may allow processing system 142 to determine if fluid is flowing from pump 102 at an acceptable or desired flow rate and, if not, to determine if there is a problem with the fluid flow such as, e.g., an occlusion in flow path 110. Processing system 142 may be configured to store each captured image such that the images may be compared to one another as well as each newly captured image.

Accordingly, display 146 may provide a visual indication of one or more conditions of pump 102 and/or infusion assembly 100. For example, display 146 may provide a graphical representation of the change in volume of fluid within chamber 126, e.g., as fluid is dispelled or dispensed from chamber 126 of pump 102. Alternatively or additionally, display 146 may provide a graphical representation of the flow rate of fluid from chamber 126, e.g., indicating whether the flow rate has increased, decreased, or remained constant. In other embodiments, display 146 may provide a numerical indication of the flow rate of fluid from pump 102, the flow rate of fluid to patient P, the volume of fluid remaining in chamber 126, the volume of fluid that has been dispensed to patient P, and/or other numerical information. In still other embodiments, display 146 may indicate the fluid is flowing from pump 102 and/or is flowing to patient P at a target or desired flow rate. Display 146 may indicate other conditions or provide other information as well.

Further, processing system 142 may assimilate data provided from one or more sources, such as the image capture feature 140 and software application of smartphone 144 as described above and/or input(s) from a caregiver or clinician. Then, processing system 142 may display such data or information derived from such data to the user, e.g., using display 146 of smartphone 144. For example, as shown schematically in FIG. 6, data or information from infusion assembly 100 may be sent to and/or captured by one or more patient or user devices 150, e.g., over or through a communications network or via a wireless relay or module as previously described. User devices 150 may comprise, e.g., a personal computing device, such as portable or wireless mobile telecommunications devices with Internet functionality, such as smartphone 144. As further examples, user devices 150 may be desktop computers, tablet computers, or any other suitable personal computing devices. In some embodiments, each user device 150 includes a control circuit having one or more processors and an associated memory device configured to perform a variety of computer-implemented functions (e.g., performing the methods, steps, calculations and the like described herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements.

Such memory device(s) may generally be configured to store suitable computer-readable instructions that, when implemented by the processor(s), configure the control circuit to perform various functions including, but not limited to, analyzing one or more images, determining one or more conditions of pump 102 and/or infusion assembly 100, or other functions as described herein. More particularly, the instructions may configure the control circuit to perform functions such as receiving directly or indirectly signals from one or more sensors (e.g., voltage sensors, current sensors, and/or other sensors) indicative of various input conditions, determining a capacitor bank voltage, controlling a pre-charge process of the capacitor bank, and/or various other suitable computer-implemented functions, which enable the processing system 142 and/or user device 150 to carry out the various functions described herein. An interface can include one or more circuits, terminals, pins, contacts, conductors, or other components for sending and receiving control signals. Moreover, the control circuit may include a sensor interface (e.g., one or more analog-to-digital converters) to permit signals transmitted from any sensors within the system to be converted into signals that can be understood and processed by the processor(s).

In one exemplary embodiment, the controller comprises a processor having a memory device storing computer executable instructions comprising machine learning techniques and the processor is adapted to execute the instructions. The machine learning techniques may include at least one of, e.g., adaptive and non-adaptive noise cancelation of noise in the signals; signal envelope detection; low pass, band-pass, band-stop, and/or high pass digital filters to extract different pump parameters from a data spectrum; or supervised or unsupervised clustering, which may include at least one of k-means, fuzzy c-means artificial neural networks, support vector machine, and/or fuzzy systems to characterize pump operation across different populations and across time (e.g., across an infusion procedure or multiple infusion procedures). Thus, in one embodiment, processing system 142, e.g., through display 146 of smartphone 144, could prompt a user to capture images of pump 102 over time and thereby, within a given interval of time, measure changes in the pump to learn if the pump is working, is working as it is intended, etc. Further, to estimate pump change over time, some statistical and morphological features such as norm, root-mean-square, skewness, kurtosis, entropy, and the like may used in a machine learning stage to compare present and past pump images. Also, machine learning based predictive models may be used, e.g., to predict when an infusion procedure may be completed.

As represented in FIG. 6, in some embodiments, user devices 150 are connected to a server 152 through a network 154 to provide and/or receive information at least from infusion assembly 100; other assemblies or medical instruments also may provide data or information to and/or receive data or information from a user device 150. For example, as described above, some embodiments of a system or method for communicating a condition of pump 102 and/or infusion assembly 100 to a user may include capturing images of pump 102 over time, storing each captured image, and comparing a newly captured or current image to one or more stored images. In such embodiments, processing system 142 may be configured to store the captured images, e.g., using one or more of the previously described memory devices, or processing system 142 may be configured to communicate with server 152 via network 154 to store the images on the server and to retrieve or utilize the stored images for comparison to one another and/or a new image. In other embodiments, server 152 may be used to store images of other infusion pumps, such as other users' pumps or exemplary pumps, and processing system 142 may be configured to compare images of pump 102 to the stored images of other infusion pumps to determine a condition of the user's pump 102. In some embodiments, processing system 142 may be configured to communication with server 152 via network 154 to execute or enable one or more machine learning techniques described above, e.g., the machine learning techniques may be applied external to processing system 142. As such, server 152 may comprise or be in communication with one or more databases for storing, accessing, and/or processing data and/or information.

It should be appreciated that network communications can comprise sending and/or receiving information over one or more networks 154 of various forms. For example, a network can comprise a dial-in network, a local area network ("LAN"), a wide area network ("WAN"), a public switched telephone network ("PSTN"), the Internet, an intranet, or other type(s) of networks. A network 154 may comprise any number and/or combination of hard-wired, wireless, or other communication links. Further, multiple medical devices or instruments such as infusion assembly 100 may be connected to server 152 via network 154 to provide and/or receive data or information. In exemplary embodiments, user devices 150 are configured to execute one or more computer programs, such as an Internet browser program, to allow users to interact with server 152, and devices 150 preferably include a display 146, such as a monitor or screen, for providing information or data to patient P, a physician, and/or a caregiver such as the flow rate of fluid from chamber 126, a change in volume of fluid, and the like.

In some embodiments, a user device 150 may utilize a mobile software application, i.e., an app, designed to capture inputs from one or more users and to provide outputs to the one or more users. For example, patient P may download the app onto his or her smartphone 144 before or after a medical procedure requiring the use of infusion assembly 100 as part of the recovery process. In some embodiments of the app, a portion of the app may be a log where patient P can provide inputs, e.g., the patient may rate his or her pain or relative pain level once a day or throughout the day, rate the patient's perceived or subjective recovery level, indicate the patient's activity level, capture an image of the patient's pump 102, or the like. The app may be tailored to the patient's specific procedure or the infusion assembly 100 the patient is using. The app may be configured to receive data or information outputs regarding infusion assembly 100, e.g., through images of pump 102 captured by the user as describe above, and to provide such data or information to the user, e.g., via display 146 incorporated into smartphone 144. In other embodiments, a web-based data collection and presentation tool rather than a mobile app may be used to gather patient-generated data and data generated by infusion assembly 100. The web-based data collection and presentation tool may be configured similarly to the above-described app, e.g., with a log portion, image processing capability, and the like. In other embodiments, one or more wired devices may be used to provide and/or receive data or information regarding infusion assembly 100. Feedback from the patient may be used to train the infusion assembly 100, e.g., for a processing system 142 having a machine learning mode, the patient may self-tune pump 102 and/or infusion assembly 100, which may be particularly useful when there is a large difference between an objective assessment of fluid that should be delivered to the patient using assembly 100 and the patient's subjective assessment, which, e.g., may be based on the patient's subjective pain level. In any event, in various embodiments, data or information from various sources may be provided to patient P or other users via a display 146 incorporated into a user device, such as user device(s) 150, which include smartphone 144. Of course, any other suitable configuration of a device having a display 146 may be used as well.

As described above, one or more captured images of pump 102 may generate a number of outputs to indicate, signal, or communicate a condition of pump 102 and/or infusion assembly 100. For example, using the captured image(s), processing system 142 may output the flow rate of fluid from expandable bladder 118. Additionally or alternatively, one output may be a volume of fluid dispensed from bladder 118 over a period of time and/or an output may be a change in the volume of fluid within chamber 126 of bladder 118 over a period of time. The one or more outputs may be communicated to a user of assembly 100—such as patient P, a physician/clinician, and/or a caregiver—using one or more visual, tactile, audible, or other signals. In particular, an output may provide information to a user via a signal such as one or more LED lights, one or more alarms, and/or a notification displayed on display 146. Other forms of data or information, and other configurations of signals for communicating such data or information, may be used as well.

Together, the pump 102, image capture device 140, and processing system 142 comprise a system for signaling a condition of infusion assembly 100, e.g., a change in volume of pump 102, a flow rate of fluid from pump 102, or the like. In some embodiments, a single user device, such as smartphone 144 or device 150, may comprise both image capture device 140 and processing system 142 such that a user may capture images and receive information regarding a condition of pump 102 and/or infusion assembly 100 with the single device. In exemplary embodiments, the single user device includes a display or screen 146 that may assist the user in utilizing the image capture feature of the device to capture an image, e.g., by providing guides 148 on the display 146, as well as supply an area in which information about pump 102 and/or infusion assembly 100 may be displayed or provided to the user.

Accordingly, a method for communicating a condition of pump 102 and/or infusion assembly 100 may include capturing an image of pump 102, processing the image, and displaying information to a user of pump 102, which communicates the condition of the pump to the user. The condition may be a change in volume of the pump 102, a flow rate of fluid from the pump 102, a flow status of the pump 102 (i.e., whether or not fluid is flowing from the pump), or the like. As previously described, capturing the image may include capturing an image of an indicator 128 on an outer layer 120 of pump 102, and processing the image may include comparing the image to a stored image. Capturing the image also may include aligning the pump 102 with guides 148 displayed on a display 146 of a user device 150 that is configured to capture images, e.g., by incorporating an image capture feature 140. Communicating the condition of the pump 102 and/or infusion assembly 100 may include displaying information, a signal, or the like on a display 146 of user device 150, as described above in greater detail. It will be understood that, as described herein, the method also may include other features, steps, or processes.

While various patents have been incorporated herein by reference, to the extent there is any inconsistency between incorporated material and that of the written specification, the written specification shall control. Further, this written description uses examples to disclose the disclosure, including the best mode, and also to enable any person skilled in the art to practice the disclosure, including making and using any devices or systems and performing any incorporated methods. The patentable scope of the disclosure is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A system for signaling a condition of an infusion assembly, the system comprising:
   an image capture device;
   a display;
   at least one processor; and
   a memory storing instructions that, when executed by the at least one processor, cause the system to:
      obtain an image of an infusion pump of the infusion assembly by the image capture device, the infusion pump comprising an expandable bladder for holding a fluid and a passive indicator visible on an outside surface of the expandable bladder, wherein the image contains the passive indicator;
      evaluate the image to determine a volume of the fluid in the infusion pump based on the passive indicator; and
      present an indication of the volume of the fluid on the display.

2. The system of claim 1, wherein the passive indicator is configured to change in size in conjunction with the expandable bladder.

3. The system of claim 1, wherein the instructions, when executed by the at least one processor, further cause the system to:
   present one or more guides on the display to assist a user in positioning the infusion pump within a field of view of the image capture device.

4. The system of claim 3, wherein the one or more guides correspond to an upper support member and a lower support member of the infusion pump such that the upper support member and the lower support member are configured to be positioned within the one or more guides prior to the obtaining of the image, the expandable bladder extending between the upper support member and the lower support member.

5. The system of claim 1, wherein the image of the infusion pump is a first image, wherein the instructions, when executed by the at least one processor, further cause the system to:
   obtain a series of additional images of the infusion pump, the series of additional images captured in succession after the obtaining of the first image; and
   store the first image and the series of additional images.

6. The system of claim 5, wherein the instructions, when executed by the at least one processor, further cause the system to:
   evaluate the first image and the series of additional images to determine a flow rate of the infusion pump; and
   present an indication of the flow rate on the display.

7. The system of claim 5, wherein the instructions, when executed by the at least one processor, further cause the system to:
   determine a change in the volume of the fluid in the infusion pump by comparing the first image with at least one image of the series of additional images; and
   present a graphical representation of the change in the volume of the fluid in the infusion pump on the display.

8. The system of claim 5, wherein the instructions, when executed by the at least one processor, further cause the system to:
   provide a prompt to a user to capture a series of additional images of the infusion pump at one or more time intervals, wherein the prompt is presented on the display or provided as an audible signal via an audio output device.

9. The system of claim 5, wherein the instructions, when executed by the at least one processor, further cause the system to:
   evaluate the first image and at least one image of the series of additional images using a machine learning model to predict when an infusion procedure will be completed.

10. The system of claim 1, wherein the instructions, when executed by the at least one processor, further cause the system to:
    present at least one of a starting volume of the infusion pump or a time interval for completing an infusion procedure on the display.

11. A method for signaling a condition of an infusion assembly, the method comprising:
    receiving, by a processing device, an image of an infusion pump of the infusion assembly captured by an image capture device, the infusion pump comprising an expandable bladder for holding a fluid and a passive indicator visible on an outside surface of the expandable bladder, wherein the image contains the passive indicator;
    evaluating the image, by the processing device, to determine a volume of the fluid in the infusion pump based on the passive indicator; and
    presenting, by the processing device, an indication of the volume of the fluid on a display.

12. The method of claim 11, wherein the passive indicator changes in size in conjunction with the expandable bladder.

13. The method of claim 11, further comprising:
    presenting one or more guides on the display to assist a user in positioning the infusion pump within a field of view of the image capture device.

14. The method of claim 13, wherein the one or more guides correspond to an upper support member and a lower support member of the infusion pump such that the upper support member and the lower support member are configured to be positioned within the one or more guides prior to the capturing of the image, the expandable bladder extending between the upper support member and the lower support member.

15. The method of claim 11, wherein the image of the infusion pump is a first image, the method further comprising:
    receiving, by the processing device, a series of additional images of the infusion pump captured by the image capture device, the series of additional images captured in succession after the capturing of the first image; and
    storing, by the processing device, the first image and the series of additional images.

16. The method of claim 15, further comprising:
evaluating, by the processing device, the first image and the series of additional images to determine a flow rate of the infusion pump; and
presenting, by the processing device, an indication of the flow rate on the display.

17. The method of claim 15, further comprising:
determining a change in the volume of the fluid in the infusion pump by comparing the first image with at least one image of the series of additional images; and
presenting a graphical representation of the change in the volume of the fluid in the infusion pump on the display.

18. The method of claim 15, further comprising:
providing a prompt, by the processing device, to a user to capture the series of additional images of the infusion pump at one or more time intervals, wherein the prompt is presented on the display or provided as an audible signal via an audio output device.

19. The method of claim 15, further comprising:
evaluating, by the processing device, the first image and at least one image of the series of additional images using a machine learning model to predict when an infusion procedure will be completed.

20. The method of claim 11, further comprising:
presenting, by the processing device, at least one of a starting volume of the infusion pump or a time interval for completing an infusion procedure on the display.

\* \* \* \* \*